(12) United States Patent
Lunde

(10) Patent No.: US 12,137,695 B2
(45) Date of Patent: Nov. 12, 2024

(54) PRODUCTION OF PAR-BAKED PRODUCTS WITH IMPROVED FRESHNESS EMPLOYING COMBINATION OF GH8 XYLANASE AND PHOSPHOLIPASE

(71) Applicant: Novozymes A/S, Bagsvaerd (DK)

(72) Inventor: Christina Lunde, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 504 days.

(21) Appl. No.: 17/434,030

(22) PCT Filed: Mar. 11, 2020

(86) PCT No.: PCT/EP2020/056496
§ 371 (c)(1),
(2) Date: Aug. 26, 2021

(87) PCT Pub. No.: WO2020/182879
PCT Pub. Date: Sep. 17, 2020

(65) Prior Publication Data
US 2022/0159975 A1    May 26, 2022

(30) Foreign Application Priority Data
Mar. 13, 2019 (EP) .................................. 19162474

(51) Int. Cl.
*A21D 8/04* (2006.01)
*A21D 10/00* (2006.01)

(52) U.S. Cl.
CPC ........... *A21D 8/042* (2013.01); *A21D 10/002* (2013.01); *C12Y 302/01008* (2013.01)

(58) Field of Classification Search
CPC .............................. A21D 8/042; A21D 10/002
See application file for complete search history.

(56) References Cited

U.S. PATENT DOCUMENTS

2012/0288585 A1* 11/2012 Beier .................... C12N 9/248
                                                                  435/252.31
2017/0303548 A1    10/2017 Krogh
2019/0008169 A1     1/2019 Mayer

FOREIGN PATENT DOCUMENTS

WO       2011/070101 A1    6/2011
WO    WO-2017131973 A1 *  8/2017 ........... A21D 10/002

OTHER PUBLICATIONS

Almeida et al., LWT—Food Science and Technology, vol. 49, No. 1, pp. 64-72 (2012).
Barcenas et al., Eur. Food Res. Technol., vol. 218, No. 1, pp. 56-61 (2003).
Bosmans et al., Food Chemistry, vol. 165, pp. 149-156 (2014).
Gerits et al., Comprehensive Reviews in Food Science and Food Safety, vol. 13, No. 5, pp. 978-989 (2014).
Sciarini et al., Food Bioprocess Technol., vol. 5, No. 5, pp. 1724-1732 (2011).

* cited by examiner

*Primary Examiner* — Jenna A Watts
(74) *Attorney, Agent, or Firm* — Yoshimi D. Barron

(57) ABSTRACT

A method of producing a par-baked product dough, comprising incorporating into the dough a phospholipase enzyme and a GH8 xylanase.

10 Claims, No Drawings
Specification includes a Sequence Listing.

SEQUENCE LISTING

```
<160> NUMBER OF SEQ ID NOS: 1

<210> SEQ ID NO 1
<211> LENGTH: 407
<212> TYPE: PRT
<213> ORGANISM: Artificial sequence
<220> FEATURE:
<223> OTHER INFORMATION: Synthetic construct

<400> SEQUENCE: 1

Ala Val His Ser Lys Thr Pro Asp Ile Leu Gly Thr Thr Gly Lys Asn
1               5                   10                  15
```

```
Asn Leu Asn Gln Ala Tyr Lys Lys Tyr Phe Asp Thr Lys Gly Asp Gly
             20                  25                  30

Lys Gly Gly Ser Leu Phe His Tyr Met Lys Asp Gly Ser Ala Tyr Ile
         35                  40                  45

Ala Ser Thr Thr Asp Asp Asn Leu Leu Gly Asn Gly Tyr Tyr Ser Val
 50                  55                  60

Lys Thr Glu Gly Met Ser Tyr Gly Met Met Ile Thr Leu Gln Met Asn
 65                  70                  75                  80

Asp Glu Tyr Lys Phe Gln Lys Leu Trp Asp Phe Val Arg Lys Tyr Met
                 85                  90                  95

Arg His Ser Asp Arg Asn Asp Ser Leu Tyr Gly Tyr His Ser Trp His
                100                 105                 110

Met Lys Thr Asn Gly Ser Asp Val Gln Thr Ile Asp Gln Asn Val Ala
             115                 120                 125

Ser Asp Gly Glu Val Trp Phe Ala Ala Ala Leu Met Met Ala Ser Gly
 130                 135                 140

Arg Trp Gly Asp Lys Lys Tyr Pro Tyr Asp Tyr Lys Ala Arg Ala Gln
145                 150                 155                 160

Asp Met Leu Asp Ala Leu Ala Gly Asp Gly Glu Tyr Ala Asn Thr Gly
             165                 170                 175

Lys Glu Ser Arg Val Phe Ile Lys Asn Ser Lys Asp Gln Arg Tyr Ala
             180                 185                 190

Met Val Arg Phe Gly Pro Tyr Val Asn Trp Thr Asp Pro Ser Tyr His
             195                 200                 205

Val Pro Ala Phe Phe Glu Leu Phe Ala Lys Ser Ala Lys Ser Ser Gln
 210                 215                 220

Gln Tyr Phe Trp Lys Asp Ala Ala Asn Lys Ser Arg Thr Tyr Leu Ser
225                 230                 235                 240

Glu Thr Thr Phe Lys Ser Val Leu Asn Asn Gly Ser Thr Val Thr Asn
             245                 250                 255

Ala Ala Thr Gly Leu Phe Pro Asp Glu Ala Gly Phe Asp Gly Val Ser
             260                 265                 270

Asp Ala Ala His Ser Ser Thr Glu Thr Asp Arg Asn Phe Ser Tyr Asp
             275                 280                 285

Ala Trp Arg Thr Val Ser His Ile Ala Met Asp His Thr Leu Trp Ser
             290                 295                 300

Ser Ala Asp Asn Ala Tyr Arg Ala Ser Glu Gln Lys Ala Val Asn Lys
305                 310                 315                 320

Phe Leu Thr Phe Met Lys Arg Glu Asn Tyr Gly Arg Thr Ala His Glu
                325                 330                 335

Tyr Thr Leu Asn Gly Thr Ala Val Lys Lys Gly Ser Pro Val Gly Leu
             340                 345                 350

Ile Ala Ala Asn Ala Gly Gly Ala Thr Ala Ala Ser Asp Ala Ser Leu
             355                 360                 365

Arg Thr Gly Phe Ala Asn Ala Phe Asn Ser Thr Tyr Ile Pro Glu Asp
370                 375                 380

Tyr Tyr Gly Ser Cys Leu Tyr Met Leu Asn Ser Leu Val Ala Asn Gly
385                 390                 395                 400

Lys Phe Ala Met Tyr Leu Pro
                405
```

PRODUCTION OF PAR-BAKED PRODUCTS WITH IMPROVED FRESHNESS EMPLOYING COMBINATION OF GH8 XYLANASE AND PHOSPHOLIPASE

CROSS-REFERENCE TO RELATED APPLICATIONS

This application is a 35 U.S.C. 371 national application of international application no. PCT/EP2020/056496 filed Mar. 11, 2020, which claims priority or the benefit under 35 U.S.C. 119 of European application no. 19162474.1 filed Mar. 13, 2019. The content of each application is fully incorporated herein by reference.

REFERENCE TO A SEQUENCE LISTING

This application contains a Sequence Listing in computer readable form, which is incorporated herein by reference. The name of the file containing the Sequence Listing is SQ.txt, which was created on Jan. 27, 2022 and has 3.67 KB.

TECHNICAL FIELD OF THE INVENTION

The present invention relates to the freshness of par-baked products. In particular, the invention relates to the field of manufacturing par-baked products using a combination of a xylanase and a phospholipase enzyme wherein the crumb softness of the par-baked products is maintained.

BACKGROUND OF THE INVENTION

When bread is stored after baking, the bread will lose its freshness within days.

In the staling process, the soft crumb becomes harder due to changes in the physical interaction of the bread components (starch, gluten, xylan, and lipids).

It is known that retrogradation of amylopection plays a major role in this staling process, but also amylose retrogradation, water migration, and changes in starch-gluten interactions are involved.

A par-baked product is a technique in which a bread or a dough product is partially baked and then typically cooled/frozen for storage. When the final dough product is desired, the par-baked product is produced by baking the product at normal baking temperatures for typically an additional 5 to 15 minutes.

For par-baked bread, the staling process is accelerated compared to a one-step baked bread. Surprisingly, the best enzymatic solution for preventing amylopection retrogradation (maltogenic alpha-amylases such as, e.g., Novamyl™), has a negative impact on the crumb firming of a par-baked product within the normal shelf life (typically 0-12 hours after the second baking).

The present invention discloses a combination of a phospholipase enzyme and a GH8 xylanase capable of maintaining a soft crumb of a par-baked product.

SUMMARY OF THE INVENTION

Surprisingly, it has been found that it is possible to maintain a soft crumb of a par-baked product, so we claim:

A method of producing a par-baked product dough, comprising incorporating into the dough a phospholipase and a GH8 xylanase, wherein the combination of the phospholipase and GH8 xylanase decreases the initial firmness of the product 1 hour after final bake-off and decreases the rate of firming of the product 3 to 7 hours after final bake-off, compared with a par-baked product dough where the phospholipase and the GH8 xylanase are not incorporated into the dough.

In one embodiment, the phospholipase is added to the dough in the range of 0.1 mg enzyme protein per kg flour to 500 mg enzyme protein per kg flour.

In one embodiment, the GH8 xylanase is added to the dough in the range of 0.01 mg enzyme protein per kg flour to 100 mg enzyme protein per kg flour.

In one embodiment, the GH8 xylanase has at least 70% identity to SEQ ID NO:1.

In one embodiment, the method according to the present invention has the following steps:
  a) the dough is made into a product,
  b) the product is baked,
  c) the product is stored, and
  d) the product is re-baked to a par-baked product.

In one embodiment, the product is stored at a temperature below 5 degrees Celsius.

In one embodiment, the flour is selected from wheat, emmer, spelt, einkorn, barley, rye, oat, corn, sorghum, rice, millet, amaranth, quinoa, cassava, or any combination thereof.

In one embodiment, the crumb firmness of the par-baked product is reduced compared with a par-baked product wherein the phospholipase enzyme and the GH8 xylanase are not added.

In one embodiment, the crumb firmness is reduced 0-8 hours after the re-baking.

In one embodiment, an alpha-amylase is additionally incorporated into the dough.

In one embodiment, we claim the use of a composition comprising a phospholipase enzyme and a GH8 xylanase for reducing the crumb firmness of a par-baked product.

In one embodiment, we claim the use of a composition comprising a phospholipase enzyme, a GH8 xylanase, and an alpha-amylase for reducing the crumb firmness of a par-baked product.

DETAILED DESCRIPTION OF THE INVENTION

Definitions

Lipase activity: Triacylglycerol lipase activity (EC 3.1.1.3), i.e., hydrolytic activity for carboxylic ester bonds in triglycerides, e.g., tributyrin.

Phospholipase activity: Phospholipase activity (A1 or A2, EC 3.1.1.32 or 3.1.1.4), i.e., hydrolytic activity towards one or both carboxylic ester bonds in phospholipids such as lecithin.

Galactolipase activity: Galactolipase activity (EC 3.1.1.26), i.e., hydrolytic activity on carboxylic ester bonds in galactolipids such as DGDG (digalactosyl diglyceride).

Fragment: The term "fragment" means a polypeptide having one or more (e.g., several) amino acids absent from the amino and/or carboxyl terminus of a mature polypeptide or domain; and wherein the fragment has xylanase enzyme activity.

Host cell: The term "host cell" means any cell type that is susceptible to transformation, transfection, transduction, or the like with a nucleic acid construct or expression vector comprising a polynucleotide of the enzyme of interest.

Mature polypeptide: The term "mature polypeptide" means a polypeptide in its final form following translation and any post-translational modifications, such as N-terminal processing, C-terminal truncation, glycosylation, phosphorylation, etc.

Sequence identity: The relatedness between two amino acid sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

(Identical Residues×100)/(Length of Alignment–Total Number of Gaps in Alignment).

Improved crumb firmness of the baked product: The term "improved crumb firmness" is defined herein as the property of a baked product that is more easily compressed compared to a baked product wherein the enzyme solution according to the invention is not added to the dough.

The crumb firmness is evaluated either empirically by the skilled test baker/sensory panel or measured by the use of a texture analyzer (e.g., TAXT2 or TA-XT Plus from Stable Micro Systems Ltd, Surrey, UK) as known in the art.

Improved flavor of the baked product: The term "improved flavor of the baked product" is evaluated by a trained test panel and/or chemical analysis (e.g., headspace GC-MS analysis). Improved flavor of the baked product comprises the reduction of off-flavor(s) of the baked product.

Improved anti-staling of the baked product: The term "improved anti-staling of the baked product" is defined herein as the properties of a baked product that have a reduced rate of deterioration of quality parameters, e.g., softness and/or elasticity, during storage.

Volume of the baked product: The term "volume of the baked product" is measured as the volume of a given loaf of bread. The volume may be determined by the rape seed displacement method.

Dough According to the Invention

The present invention relates to a process for producing par-baked food products comprising incorporating into the flour or dough ingredients a phospholipase enzyme and a GH8 xylanase.

The phrase "incorporating into the dough" is defined herein as adding the enzymes according to the invention to the dough, to any ingredient from which the dough is to be made, and/or to any mixture of dough ingredients from which the dough is to be made.

In other words, the enzymes according to the invention may be added in any step of the dough preparation and may be added in one, two or more steps. The enzymes are added to the ingredients of dough that may be kneaded and processed as known in the art for par-baked products.

The term "effective amount" is defined herein as an amount of an enzyme composition according to the invention that is sufficient for providing a measurable effect on at least one property of interest of the dough and/or baked product.

The term "dough" is defined herein as a mixture of flour and other baking ingredients firm enough to knead or roll. In the context of the present invention, batters are encompassed in the term "dough".

The dough of the invention may comprise flour derived from any cereal grain or other sources, including wheat, emmer, spelt, einkorn, barley, rye, oat, corn, sorghum, rice, millet, amaranth, quinoa, cassava, and any combination thereof.

The dough may also comprise other conventional dough ingredients, e.g., proteins, such as milk powder, gluten, and soy; eggs (either whole eggs, egg yolks, or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate, or calcium sulfate, and/or an emulsifier.

The dough may comprise fat (triglyceride) such as granulated fat or shortening.

The dough of the invention is normally a leavened dough or a dough to be subjected to leavening.

The dough may be leavened in various ways, such as by adding chemical leavening agents, e.g., baking powder, sodium bicarbonate, or by adding a leaven (fermenting dough), but it is preferred to leaven the dough by adding a suitable yeast culture, such as a culture of *Saccharomyces cerevisiae* (baker's yeast), e.g., a commercially available strain of *S. cerevisiae*.

The amount of phospholipase enzyme according to the invention may be between 0.1-500 mg enzyme protein per kg flour in the dough, in particular 0.1-100 mg enzyme protein per kg flour, in particular 0.1-10 mg enzyme protein per kg flour.

The amount of the GH8 xylanase according to the invention may be between 0.01-100 mg enzyme protein per kg flour in the dough, in particular 0.01-10 mg enzyme protein per kg flour, in particular 0.01-1 mg enzyme protein per kg flour.

Sources of Phospholipase Enzymes

The phospholipase enzymes may be prokaryotic, particularly bacterial, or eukaryotic, e.g., from fungal or animal sources.

Phospholipase enzymes may be derived, e.g., from the following genera or species: *Thermomyces, T. lanuginosus* (also known as *Humicola lanuginosa*); *Humicola, H. insolens; Fusarium, F. oxysporum, F solani, F. heterosporum; Aspergillus, A. tubigensis, A. niger, A. oryzae; Rhizomucor; Candida, C. antarctica, C. rugosa, Penicillium, P. camembertii; Rhizopus, Rhizopus oryzae; Absidia, Dictyostelium, Mucor, Neurospora, Rhizopus, R. arrhizus, R. japonicus, Sclerotinia, Trichophyton, Whetzelinia, Bacillus, Citrobacter, Enterobacter, Edwardsiella, Erwinia, Escherichia, E. coli, Klebsiella, Proteus, Providencia, Salmonella, Serratia, Shigella, Streptomyces, Yersinia, Pseudomonas*, or *P. cepacia*.

The phospholipase enzyme may be produced in a suitable host cell as known in the art.

Phospholipase may also be obtained from bee or snake venom or from mammal pancreas, e.g., porcine pancreas.

WO 98/26057 discloses a lipase/phospholipase from *Fusarium oxysporum* and its use in baking.

WO 2004/099400 discloses various phospholipase enzymes and their use in baking for reduction of dough stickiness.

Suitable commercial phospholipase preparations are Lipapan F™, Lipopan Xtra™, and Lipopan Prime™ (available from Novozymes A/S).

Other available phospholipases are, e.g., Panamore™ available from DSM.

Commercial lipase preparations are, e.g., Lipopan 50 BG™ available from Novozymes A/S.

Xylanases

Xylanases are classified as EC 3.2.1.8 according to enzyme nomenclature.

Xylanases may be of microbial origin, e.g., derived from a bacterium or fungus, such as a strain of *Aspergillus*, in particular of *A. aculeatus, A. niger, A. awamori*, or *A. tubigensis*, from a strain of *Trichoderma*, e.g., *T. reesei*, or from a strain of *Humicola*, e.g., *H. insolens*.

According to the present invention, a GH8 xylanase is preferred. The GH8 xylanase may be produced in a suitable host cell as known in the art.

GH8 xylanases are described in, e.g., WO 2004/023879 and WO 2011/070101.

In a preferred embodiment, the GH8 xylanase has at least 70% sequence identity with mature GH8 shown in SEQ ID NO:2 of WO 2019/122083.

For purposes of the present invention, the polypeptide disclosed in SEQ ID NO:2 of WO 2019/122083 is used to determine the corresponding amino acid residue in another GH8 xylanase enzyme.

The amino acid sequence of another GH8 xylanase is aligned with the polypeptide disclosed in SEQ ID NO:2 of WO 2019/122083, and based on the alignment, the amino acid position number corresponding to any amino acid residue in the polypeptide disclosed in SEQ ID NO:2 of WO 2019/122083 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

In one embodiment, the GH8 xylanase according to the invention has at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO:2 of WO 2019/122083.

The GH8 xylanase of the present invention preferably comprises or consists of the amino acids in SEQ ID NO:2 of WO 2019/122083; or is an allelic variant thereof; or is a fragment thereof having xylanase enzyme activity.

In another embodiment, the present invention relates to variants of the polypeptide of SEQ ID NO:2 of WO 2019/122083 comprising a substitution, deletion, and/or insertion at one or more (e.g., several) positions. In an embodiment, the number of amino acid substitutions, deletions and/or insertions introduced into the polypeptide of SEQ ID NO:2 of WO 2019/122083 is not more than 20, e.g., 1, 2, 3, 4, 5, 6, 7, 8, 9, 10, 11, 12, 13, 14, 15, 16, 17, 18, or 19.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Suitable commercially available GH8 xylanase preparations for use in the present invention include PANZEA BG™ (available from Novozymes A/S), Additional Enzymes Optionally, one or more additional enzymes such as aminopeptidase, amylase, alpha-amylase, beta-amylase, carboxypeptidase, catalase, chitinase, cutinase, glycosyltransferase, deoxyribonuclease, esterase, galactanase, glucan 1,4-alpha-maltotetrahydrolase, glucanase, alpha-galactosidase, beta-galactosidase, glucoamylase, alpha-glucosidase, beta-glucosidase, haloperoxidase, invertase, laccase, mannanase, mannosidase, oxidase, pectinolytic enzymes, peptidoglutaminase, peroxidase, phytase, polyphenoloxidase, proteolytic enzyme, ribonuclease, and/or transglutaminase may be used together with the phospholipase enzyme and the GH8 xylanase according to the invention.

Preferably, an alpha-amylase is added together with the phospholipase enzyme and the GH8 xylanase according to the invention.

The alpha-amylase may be fungal or bacterial, e.g., an alpha-amylase from *Bacillus*, e.g., *B. licheniformis* or *B. amyloliquefaciens*, or a fungal alpha-amylase, e.g., from *A. oryzae*.

Suitable commercial fungal alpha-amylase compositions include, e.g., BAKEZYME P 300 (available from DSM) and FUNGAMYL 2500 SG, FUNGAMYL 4000 BG, FUNGAMYL 800 L, FUNGAMYL ULTRA BG and FUNGAMYL ULTRA SG (available from Novozymes A/S).

A protease may also be added; the protease may be from *Bacillus*, e.g., *B. amyloliquefaciens* or from *Thermus aquaticus*.

The glucoamylase include glucoamylases having a sequence identity of at least 50%, at least 60%, at least 65%, at least 70%, at least 75%, at least 80%, at least 85%, at least 90%, at least 95%, at least 96%, at least 97%, at least 98%, or at least 99% to the amino acid sequence of the *A. niger* G1 or G2 glucoamylase (Boel et al. (1984), EMBO J. 3 (5), p. 1097-1102), the *A. awamori* glucoamylase disclosed in WO 84/02921, or the *A. oryzae* glucoamylase (Agric. Biol. Chem. (1991), 55 (4), p. 941-949).

The glucose oxidase may be a fungal glucose oxidase, in particular an *Aspergillus niger* glucose oxidase (such as GLUZYME™, available from Novozymes A/S).

Enzyme Preparation

The enzymes according to the present invention are preferably prepared in the form of a granulate or agglomerated powder. They preferably have a narrow particle size distribution with more than 95% (by weight) of the particles in the range from 25 to 500 μm.

Granulates and agglomerated powders may be prepared by conventional methods, e.g., by spraying the enzyme onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

The enzymes may also be prepared in liquid forms.

Par-Baked Products

Par-baked is a technique in which a bread or a dough product is partially baked and then typically rapidly cooled/frozen for storage.

The raw dough is baked normally, but halted at about approximately 80% of the normal cooking time, where after it is rapidly cooled.

A par-baked dough product bread can be transported easily, and stored until needed. Par-baked dough products are kept in sealed containers that prevent moisture loss. They are may be stored at room temperature; or stored in a fridge, or stored in a freezer.

The freezing step may lead to ice crystal formation and subsequent damage to the starch granules and amylose leakage. It is therefore likely that the amount of leaked amylose and unbound water is higher prior to the second bake-off than in a bread baked without a freezing step. These are two parameters known to increase the crumb firming rate.

When the final dough product is desired, a par-baked product is "finished off" by baking it at normal temperatures for an additional time, typically 5 to 15 minutes. The exact time must be determined by testing, as the time varies depending on the product.

Accordingly, the par-baked product is manufactured by the following steps:

a) the dough is made into a product,
b) the product is baked,
c) the product is stored, and
d) the product is re-baked to a par-baked product.

The product may be stored at ambient/room temperature, or the product may be stored a low temperature, which means that it will normally be stored at a temperature below 5 degrees Celsius. In one embodiment, the product will be stored in a freezer.

Bread Improvers and Patisserie Mixes or Premixes

The phospholipase enzyme and the GH8 xylanase of the present invention may advantageously be part of a bread improver or a patisserie mix or a premix.

"Bread improvers" (also referred to as "dough conditioners" or "dough improvers" or "improving agents" or "flour treatment agents") are typically added to the dough in order to improve texture, structure, volume, flavour and freshness of the baked product as well as to improve machinability and stability of the dough.

Typically, a bread improver may comprise one or more enzyme(s), one or more oxidizing or reducing agent(s) (such as, e.g., ascorbic acid, glutathione, cysteine), one or more emulsifier(s) (such as, e.g., diacetyl tartaric acid esters of monoglycerides (DATEM), sodium stearoyl lactylate (SSL), calcium stearoyl lactylate (CSL), glycerol monostearate (GMS), rhamnolipids, lecithins, sucroesters, bile salts), one or more lipid material(s) (such as, e.g., butter, oil, shortening), one or more sugar(s), one or more flours or flour fraction(s), one or more vitamin(s) (such as, e.g., pantothenic acid and vitamin E), one or more gum(s), and/or one or more source(s) of fibre (such as, e.g., oat fibre).

Cake (patisserie) mixes typically comprise all the ingredients of a cake recipe with the exception of water, fat (oil, butter, margarine), and eggs. Eggs may be added in a cake (patisserie) mix in a powder form. Cake (patisserie) premixes are typically cake mixes where all or part of the flour and sugar has been removed.

Par-Baked Products

The process of the invention may be used for any kind of par-baked product prepared from dough, in particular of a soft character, either of a white, light or dark type.

Examples are bread (in particular white, whole-meal or rye bread), typically in the form of loaves or rolls, bread, flat bread, pita bread, tortillas, cakes, pancakes, biscuits, wafers, cookies, pie crusts, pizza, and the like.

EXAMPLES

Example 1

Par-Baked Bread from Dough with Novamyl 3D™

Dough was prepared from the basic ingredients detailed in Table 1 with the addition of the maltogenic alpha-amylase (Novamyl 3D BG) as described in Table 2. In addition to Novamyl 3D, all doughs contained 15 ppm Fungamyl 2500 SG.

TABLE 1

| Dough ingredients: | |
| --- | --- |
| Ingredients | Wt % |
| Whole wheat flour[*)] | 60.3 |
| Water | 36.1 |
| Yeast | 1.5 |
| Salt | 0.9 |
| Oil | 1.2 |

[*)]Commercial wheat flour (Meneba Kolibri) treated with ascorbic acid + 15 ppm Fungamyl 2.500 SG The dough was mixed in a spiral mixer (Diosna, 370 mm bowl) at 17 rpm for 3 minutes, and 35 rpm for 7 minutes (speed of the spiral rotor). The dough temperature during mixing was 26° C.

The initial dough was divided into 1900 g and rounded into 30 rolls using a roll rounder (Rotamaten, Werner & Pfleiderer). The rolls were allowed to rise for 60 minutes at 32° C. and 82% relative humidity. The dough was subsequently baked for 17 minutes at 230° C. in a Piccolo oven with steam.

After baking, the rolls were allowed to cool to room temperature for 30 minutes and then frozen in a blast freezer (Tecnomac) at −18° C. for 40 minutes. The frozen rolls were wrapped in plastic and stored in a minus 18° C. freezer for 1-2 weeks. Final bake-off was done in a rack oven at 190° C. for 5 minutes.

Texture Analysis Method

Firmness was measured 1, 3 and 7 hours after bake-off using a TA-XT plus texture analyzer fitted with a spherical ball probe (1" diameter, TA-18B, Stable Micro Systems, Godalming, UK).

For each time point, firmness was measured on 5 separate rolls with 3 measurements taken from each roll. Thus, for each time point, the firmness values were an average of the 15 measurements taken. Each roll was prepared by cutting the roll parallel with and 1.4 cm above the bottom. The measurements were done at 3 different places on the crumb, preferably 1.5 cm from the crust by turning the sample 120° after each measurement.

Measurements of firmness were conducted as follows:

The crumb was compressed 40% with a speed of 1.7 mm/sec, and a 5 gram trigger point. The force (g) at 25% compression was taken as the firmness of the sample.

Results

The rolls were evaluated using the Texture Analyzer 1, 3, and 7 hours after final bake-off.

The rolls prepared from dough with Novamyl 3D BG showed an increase in the initial crumb firmness as compared to the control without additional enzymes (Table 2).

Table 2 shows that after 3 and 7 hours, the crumb firmness was still significantly higher in the rolls with Novamyl 3D BG than in the control. Hence, Novamyl 3D promotes crumb firming and does not prevent staling of the par-baked rolls.

TABLE 2

Change in firmness (g-force) with storage time after final bake-off of roll with Novamyl 3D BG (MANU/kg flour)

| Enzyme | 1 hour | 3 hours | 7 hours |
|---|---|---|---|
| Control | 48 | 54 | 69 |
| Novamyl 3D BG (750 MANU/kg) | 66 | 75 | 79 |
| Novamyl 3D BG (1500 MANU/kg) | 67 | 78 | 78 |

Example 2

Par-Baked Bread from Dough with GH11 Xylanase and Phospholipase

Par-baked rolls were prepared as described in Example 1, but instead of Novamyl 3D, a GH11 xylanase (Pentopan Mono™) and/or a phospholipase (Lipopan Prime™) were added to the dough ingredients.

The firmness of the par-baked rolls were determined as described in Example 1.

Results

It can be seen from Table 3 that the rolls prepared from dough with a GH11 xylanase or a phospholipase showed a lower initial softness (1-3 hours) than the control.

Combining the GH11 xylanase and the phospholipase did, however, not give any further decrease in firmness as compared to the phospholipase on its own. After 3-7 hours, a similar firmness was obtained with the GH11 xylanase and phospholipase combination, as the phospholipase alone (Table 3).

TABLE 3

Change in firmness (g-force) with storage time after final bake-off of a roll with G11 xylanase (mg EP/kg flour) and phospholipase (mg EP/kg flour)

| Enzyme | 1 hour | 3 hours | 7 hours |
|---|---|---|---|
| Control | 74 | 88 | 94 |
| Pentopan Mono (0.4 mg EP/kg) | 61 | 60 | 89 |

TABLE 3-continued

Change in firmness (g-force) with storage time after final bake-off of a roll with G11 xylanase (mg EP/kg flour) and phospholipase (mg EP/kg flour)

| Enzyme | 1 hour | 3 hours | 7 hours |
|---|---|---|---|
| Lipopan Prime (0.6 mg EP/kg) | 54 | 57 | 79 |
| Lipopan Prime (0.6 mg EP/kg) & Pentopan Mono (0.4 mg EP/kg) | 58 | 62 | 80 |

Example 3

Par-Baked Bread from Dough with GH8 Xylanase and Phospholipase

Par-baked rolls were prepared as described in Example 1, but instead of Novamyl 3D, a GH8 xylanase (Panzea™) and/or a phospholipase (Lipopan Prime™) were added to the dough ingredients.

The firmness of the par-baked rolls was determined as described in Example 1.

Results

It can be seen from Table 4 that adding a GH8 xylanase to the dough gives a lower initial firmness than the control. The firmness after 1 to 3 hours was not lower for the combination than for the GH8 xylanase or phospholipase alone.

Surprisingly, the rolls prepared from a dough with a GH8 xylanase and a phospholipase combination showed a significant difference in firmness after 3 h as compared with the GH8 xylanase or phospholipase alone.

This shows that the combination of a GH8 xylanase and a phospholipase not only affects the initial firmness, but also impacts the rate of firming from 3-7 hours (Table 4). This is not observed for the phospholipase and the xylanase alone.

TABLE 4

Change in firmness (g-force) with storage time after final bake-off of a roll with GH8 xylanase (mg EP/kg flour) and phospholipase (mg EP/kg flour)

| Enzyme | 1 hour | 3 hours | 7 hours |
|---|---|---|---|
| Control | 71 | 81 | 94 |
| Panzea (0.06 mg EP//kg) | 55 | 54 | 77 |
| Lipopan Prime (0.6 mg EP/kg) | 66 | 69 | 86 |
| Lipopan Prime (0.6 mg EP/kg) & Panzea (0.06 mg EP/kg) | 55 | 60 | 63 |

The invention claimed is:

1. A method of producing a par-baked product, comprising
   a) providing a dough comprising a phospholipase and a GH8 xylanase,
   b) making the dough into a product,
   c) partially baking the product,
   d) cooling the par-baked product, and
   e) storing the par-baked product,
   wherein the par-baked product produces a baked product with reduced crumb firmness compared to a par-baked product where the phospholipase and the GH8 xylanase are not incorporated into the dough.

2. The method according to claim 1, wherein the phospholipase is incorporated into the dough in the range of 0.1 mg enzyme protein per kg flour to 500 mg enzyme protein per kg flour.

3. The method according to claim 1, wherein the GH8 xylanase is incorporated into the dough in the dose range of 0.01 mg enzyme protein per kg flour to 100 mg enzyme protein per kg flour.

4. The method according to claim 1, wherein the dough comprises flour selected from wheat, emmer, spelt, einkorn, barley, rye, oat, corn, sorghum, rice, millet, amaranth, *quinoa*, cassava, or any combination thereof.

5. The method according to claim 1, wherein additionally an alpha-amylase is incorporated into the dough.

6. The method according to claim 1, wherein the GH8 xylanase has at least 85% sequence identity to the amino acid sequence of SEQ ID NO: 1.

7. The method according to claim 1, wherein the par-baked product is stored at room temperature, in a refrigerator, or frozen.

8. A method of producing a baked product, comprising
   a) providing a dough comprising a phospholipase and a GH8 xylanase,
   b) making the dough into a product,
   c) partially baking the product,
   d) cooling the par-baked product,
   e) storing the par-baked product, and
   f) re-baking the par-baked product to produce a baked product,
   wherein the crumb firmness of the baked product is reduced compared to a baked product where the phospholipase and the GH8 xylanase are not incorporated into the dough.

9. The method of claim 8, wherein the combination of the phospholipase and GH8 xylanase decreases the initial firmness of the baked product 1 hour after final bake-off and decreases the rate of firming of the baked product 3 to 7 hours after final bake-off, compared with where the phospholipase and the GH8 xylanase are not incorporated into the dough.

10. The method according to claim 8, wherein the crumb firmness is reduced 0-8 hours after the re-baking.

* * * * *